United States Patent
Campbell et al.

(10) Patent No.: US 8,778,856 B2
(45) Date of Patent: Jul. 15, 2014

(54) LOW TEMPERATURE PERFORMANCE LUBRICATING OIL DETERGENTS AND METHOD OF MAKING THE SAME

(75) Inventors: Curtis Bay Campbell, Hercules, CA (US); Gilles P. Sinquin, Saint Martin du Manoir (FR); Jean-Louis Le Coent, Le Havre (FR); Jan Anthony Burval, San Rafael, CA (US)

(73) Assignees: Chevron Oronite Company LLC, San Ramon, CA (US); Chevron Oronita S.A., Cedex (FR)

( * ) Notice: Subject to any disclaimer, the term of this patent is extended or adjusted under 35 U.S.C. 154(b) by 73 days.

(21) Appl. No.: 12/629,349

(22) Filed: Dec. 2, 2009

(65) Prior Publication Data

US 2011/0130315 A1    Jun. 2, 2011

(51) Int. Cl.
  C10M 159/22    (2006.01)
  C07C 69/88    (2006.01)
(52) U.S. Cl.
  USPC ............................................. 508/460; 560/71
(58) Field of Classification Search
  USPC ...................................... 508/460, 391; 560/71
  See application file for complete search history.

(56) References Cited

U.S. PATENT DOCUMENTS

| | | | |
|---|---|---|---|
| 4,045,507 A | 8/1977 | Cupples et al. | |
| 4,238,343 A | 12/1980 | Pellegrini, Jr. | |
| 5,322,529 A * | 6/1994 | Buckley, III | 44/387 |
| 5,895,777 A | 4/1999 | Ueda et al. | |
| 2007/0027043 A1 | 2/2007 | Le Coent | |
| 2007/0027044 A1 | 2/2007 | Le Coent | |
| 2009/0170737 A1 * | 7/2009 | Campbell et al. | 508/460 |

FOREIGN PATENT DOCUMENTS

| | | |
|---|---|---|
| CN | 1708471 A | 12/2005 |
| EP | 1154012 | 5/2008 |
| GB | 734598 | 8/1955 |
| GB | 734622 | 9/1955 |
| GB | 738359 | 10/1955 |
| GB | 786167 | 11/1957 |
| GB | 1146925 | 3/1969 |

OTHER PUBLICATIONS

BF3-Catalyzed Oligomerization of Alkenes (Structures, Mechanisms and Properties), 183rd ACS Natl. Meet. (Las Vegas, Mar. 1982). Ind. Eng. Chem., Prod. Res. Dev., 22(2), 182-91 (Jun. 1983).
API Publicarion 1509, 14th Edition, Addendum I. Dec. 1998.
Totten, George, E., Fuels and Lubricants Handbook: Technology, Properties, Performance and Testing, 2003, pp. 203-211.
Chevron Oronite Detergents https://www.oronite.com/products/detergents.asp, (2013).

* cited by examiner

*Primary Examiner* — Cephia D Toomer
*Assistant Examiner* — Vishal Vasisth

(57) ABSTRACT

A carboxylate detergent prepared by the process comprising (a) alkylating a hydroxyaromatic compound with at least one alpha olefin oligomer, derived from $C_8$ to $C_{20}$ alpha olefins, to thereby produce an alkylhydroxyaromatic compound, and wherein at least 90% of the molecules in the alkylhydroxyaromatic compound have the alkyl group attached at the 4-position or higher from the terminus of the longest chain of the alkyl group, and further wherein the alkyl group comprises at least one hydrocarbon tail of at least 7 carbons; (b) neutralizing the resulting alkylated hydroxyaromatic compound with an alkali metal base; (c) carbonating the alkali metal salt from step (b) with carbon dioxide; (d) acidifying the salt produced in step (c); and (e) overbasing the resulting alkylated hydroxyaromatic carboxylic acid.

11 Claims, No Drawings

LOW TEMPERATURE PERFORMANCE LUBRICATING OIL DETERGENTS AND METHOD OF MAKING THE SAME

FIELD OF THE INVENTION

The present invention is directed to low temperature performance lubricating oils and a method of making the same. These detergents exhibit superior performance at low temperatures.

BACKGROUND OF THE INVENTION

Overbased detergents are well described to provide lubricating properties. Often such detergent additives are proportioned with other lubricating additives to provide lubricating oil compositions that exhibit certain desired lubricating properties.

Alkaline-earth metal hydroxybenzoates are also known as additives for engine lubricating oils.

DESCRIPTION OF THE RELATED ART

U.S. Pat. No. 5,895,777 describes lubricating oil additives comprising the alkaline-earth metal salts of aromatic carboxylic hydroxy acids containing carboxylic acids having 16 to 36 carbon atoms.

U.S. Patent Application Publication No. US 2007/0027044 describes a process for preparing an overbased alkali metal alkylhydroxybenzoate, said process comprising overbasing an alkali metal alkylhydroxybenzoate or a mixture of alkali metal alkylhydroxybenzoate and up to 50 mole % of alkylphenol, based on the total mixture of alkylhydroxybenzoate and alkylphenol, with a molar excess of alkaline earth metal base and at least one acidic overbasing material in the presence of at least one carboxylic acid having from one to four carbon atoms and a solvent selected from the group consisting of aromatic hydrocarbons, aliphatic hydrocarbons, monoalcohols and mixtures thereof.

European Patent Application No. 1,154,012 describes lubricating compositions comprising an oil, an anti-wear additive and a sole oil-soluble overbased detergent comprising an aromatic carboxylate, such as a calcium salicylate substituted by a hydrocarbon remainder.

British Patent No. 1,146,925 describes lubricating compositions comprising, as lubricating agents, polyvalent metal salts, in particular calcium, and alkylsalicylic acids comprising more than 12, preferably 14 to 18 carbon atoms in the alkyl group. These salts can be prepared from the corresponding sodium salts, as synthesis intermediates.

British Patent No. 786,167 describes polyvalent metal salts of oil-soluble organic acids, such as sulfonic hydrocarbons, naphthenic acids or alkylhydroxybenzoic acids, in particular alkylsalicylic acids having an alkyl radical of up to 22 carbon atoms. The alkylsalicylic acids can be prepared from sodium alkylsalicylic acids according to the processes described in British Patents Nos. 734,598; 734,622 and 738,359. The sodium alkylsalicylates described in these British patents are useful as synthetic intermediates for the preparation of alkaline-earth alkylsalicylates, which are also useful as additives for lubricating oil.

In general, the above references describe processes for aromatic hydroxy carboxylic acids and their salts which are derived from alkaline salts of phenol derivatives, such as phenol itself, cresols, mono- and dialkylphenols, the alkyl group having from about 8 to 18 carbon atoms, halogenated phenols, aminophenols, nitrophenols, 1-naphthol, 2-naphthol, halogenated naphthols, and the like. The processes described above, however, lead to products having high sediment content at high TBN that decrease product yield and create added disposal expense. Thus, it is desirable to have a process that improves product yield by minimizing the sediment resulting from such processes.

SUMMARY OF THE INVENTION

In one embodiment, the present invention is directed to a carboxylate detergent prepared by the process comprising
(a) alkylating a hydroxyaromatic compound with at least one alpha olefin oligomer, derived from $C_8$ to $C_{20}$ alpha olefins, to thereby produce an alkylhydroxyaromatic compound, and wherein at least 90% of the molecules in the alkylhydroxyaromatic compound have the alkyl group attached at the 4-position or higher from the terminus of the longest chain of the alkyl group, and further wherein the alkyl group comprises at least one hydrocarbon tail of at least 7 carbons;
(b) neutralizing the resulting alkylated hydroxyaromatic compound with an alkali metal base to provide an alkali metal salt of the alkylated hydroxyaromatic compound;
(c) carbonating the alkali metal salt from step (b) with carbon dioxide thereby producing an alkylated hydroxyaromatic carboxylic acid alkali metal salt;
(d) acidifying the salt produced in step (c) with acid to produce the alkylated hydroxyaromatic carboxylic acid; and
(e) overbasing the alkylated hydroxyaromatic carboxylic acid with lime in the presence of carbon dioxide thereby producing an overbased alkylated hydroxyaromatic carboxylate detergent.

In another embodiment, the present invention it directed to a carboyxlate detergent having the following structure:

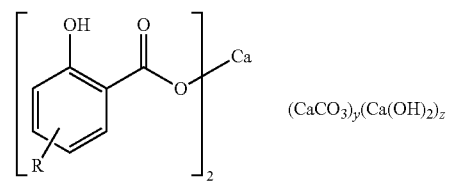

wherein R is a substantially straight-chain alkyl group of from about 16 to 40 carbon atoms, wherein the alkyl group is derived from substantially straight chain oligomers of $C_8$ to $C_{20}$ alpha olefins, and wherein at least 90% of the substantially straight-chain alkyl group has the alkyl group attached at the 4-position or higher from the terminus of the longest chain of the alkyl group, and further wherein the alkyl group comprises at least one hydrocarbon tail of at least 7 carbons and wherein y and z are independently whole or partial integers.

DETAILED DESCRIPTION OF THE INVENTION

While the invention is susceptible to various modifications and alternative forms, specific embodiments thereof are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

Definitions

Metal—The term "metal" refers to alkali metals, alkaline earth metals, or mixtures thereof.

Alkali Metal Base—The term "alkaline metal base" refers to potassium, sodium, lithium or mixtures thereof.

Olefins—The term "olefins" refers to a class of unsaturated aliphatic hydrocarbons having one or more carbon-carbon double bonds, obtained by a number of processes. Those containing one double bond are called mono-alkenes, and those with two double bonds are called dienes, alkyldienes, or diolefins. Alpha olefins are particularly reactive because the double bond is between the first and second carbons. Examples are 1-octene and 1-octadecene, which are used as the starting point for medium-biodegradable surfactants. Linear and branched olefins are also included in the definition of olefins.

Linear Olefins—The term "linear olefins," which include normal alpha olefins and linear alpha olefins, refers to olefins which are straight chain, non-branched hydrocarbons with at least one carbon-carbon double bond present in the chain.

The term "alpha olefin" or "simple alpha olefin" as used herein refers generally to 1-olefins, wherein the double bond is at the terminal position of an alkyl chain. Alpha olefins are almost always mixtures of isomers and often also mixtures of compounds with a range of carbon numbers. Low molecular weight alpha olefins, such as the $C_6$, $C_8$, $C_{10}$, $C_{12}$ and $C_{14}$ alpha olefins, are almost exclusively 1-olefins. Higher molecular weight olefin cuts such as $C_{16-18}$ or $C_{20-24}$ have increasing proportions of the double bond isomerized to an internal or vinylidene position; nonetheless these higher molecular weight cuts are also called alpha olefins herein.

The term "alpha olefin oligomer(s)" (AOO), as used herein means olefin dimers, trimers, tetramers and pentamers and mixtures thereof prepared or derived from $C_8$ to $C_{20}$ alpha olefins. The olefin double bond of these AOO's is generally located at least n–4 carbon atoms from the end of the longest carbon chain, where n is the number of carbon atoms in the starting alpha olefin.

The term "substantially straight-chained" is meant to designate an alkyl group. The term "hydroxyaromatic compounds" are used interchangeably with alkylphenol(s).

Carboxylate Detergent

One embodiment of the present invention is directed to a carboxylate detergent having the following structure:

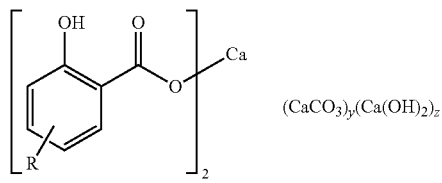

wherein R is a substantially straight-chain alkyl group of from about 16 to 40 carbon atoms, wherein the alkyl group is derived from substantially straight chain oligomers of $C_8$ to $C_{20}$ alpha olefins, and wherein the alkyl group is attached to the phenol ring at least 4 carbon atoms from the terminus of the longest chain of the alkyl group, and further wherein the alkyl group comprises at least one hydrocarbon tail of at least 7 carbons and wherein y and z are independently whole or partial integers.

Process for Preparing the Carboxylate

The present invention is directed to a carboxylate detergent which is prepared by the process described herein.

In one embodiment, the carboxylate detergent is prepared by (1) neutralizing an alkylated hydroxyaromatic compound with an alkali metal base thereby producing a neutralized alkylated hydroxyaromatic compound which is then (2) carboxylated by bubbling carbon dioxide ($CO_2$) into the neutralized alkylated hydroxyaromatic compound until at least 50% of the starting alkylated hydroxyaromatic compound has been converted to alkylhydroxybenzoic acid thereby resulting in an alkylated hydroxyaromatic carboxylic acid alkali metal salt which is then (3) contacted with at least one acid capable of converting the alkali metal salt to an alkylated hydroxyaromatic carboxylic acid and which is (4) overbased to produce an overbased alkylated hydroxyaromatic carboxyate detergent.

The specific processes steps are outlined herein below.

Hydroxyaromatic Compound

At least one hydroxyaromatic compound or a mixture of hydroxyaromatic compounds may be used for the alkylation reaction in the present invention. Preferably the at least one hydroxyaromatic compound or the hydroxyaromatic compound mixture comprises at least one of monocyclic hydroxyaromatics, such as phenol, cresol, or mixtures thereof. The at least one hydroxyaromatic compound or hydroxyaromatic compound mixture may also comprise bi-cyclic and poly-cyclic hydroxyaromatic compounds, such as 2-naphthol. More preferably, the at least one hydroxyaromatic compound or hydroxyaromatic compound mixture is phenol, including all isomers.

Alpha Olefin Oligomer

At least one alpha olefin oligomer, derived from $C_8$ to $C_{20}$ alpha olefins, is reacted with the at least one hydroxyaromatic compound thereby producing an alkylated hydroxyaromatic compound. Furthermore, at least 90% of the molecules in the alkylhydroxyaromatic compound have the alkyl group attached at the 4-position or higher from the terminus of the longest chain of the alkyl group, and the alkyl group comprises at least one hydrocarbon tail of at least 7 carbons. Preferably, at least 95% of the molecules in the alkylhydroxyaromatic compound have the alkyl group attached at the 4-position or higher form the terminus of the longest chain of the alkyl group, and the alkyl group comprises at least one hydrocarbon tail of at least 7 carbons.

Alkylation with alpha olefin oligomers, such as decene trimer or octene tetramer, provides alkylphenols having "pinwheel" configurations. By "pinwheel" configuration is meant that the alkyl group is attached, for example to an aromatic ring, at a position significantly removed from the terminus of the longest chain of the alkyl group. This results in at least two hydrocarbon tails, or wheels of the pinwheel, emanating from near the attachment point. By "significantly removed from the terminus" is meant at least 4 carbon atoms from the terminus of the longest chain of the alkyl group, preferably at least 6 carbon atoms from the terminus of the longest chain of the alkyl group, more preferably at least 8 carbon atoms toward the center of the chain. Thus a "pinwheel" alkyl phenol has an alkyl group comprising at least two tails of at least six carbon atoms, preferably at least 7 carbon atoms.

Preferred "pinwheel" compounds useful in this invention are those wherein the alkyl substituent has tails which are substantially straight-chain hydrocarbon radicals.

Such pinwheel configurations can be represented by structure C as an example of decene dimer-derived alkylhydroxyaromatic compounds and structure D as an example of decene trimer-derived alkylhydroxyaromatic compounds, as shown below. In these structures, the brackets are intended to denote the various manners of attachment of the alkyl group to the phenol.

Structure C

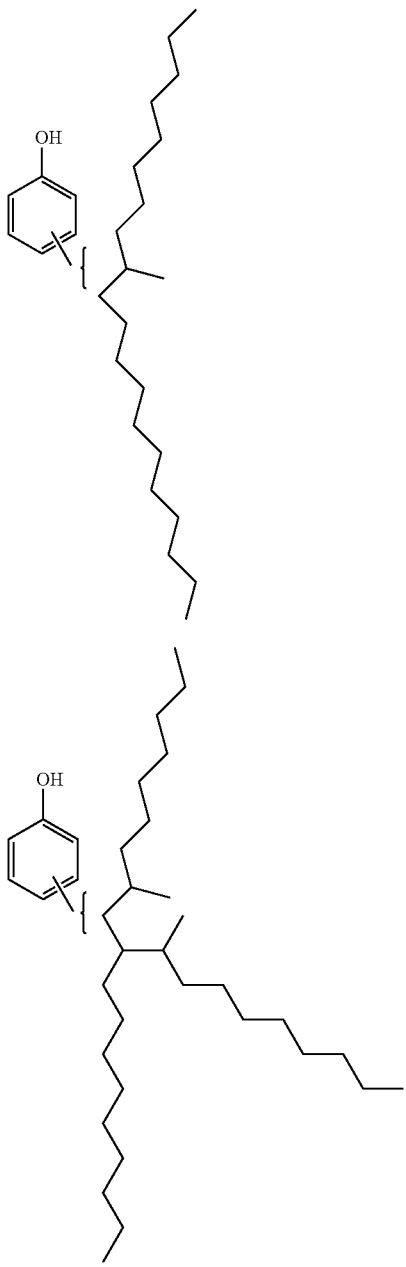

Structure D

The alpha olefin oligomers used herein are prepared by methods well-known in the art. One preferred method of preparing these oligomers is using $BF_3$ as the oligomerization catalyst, as described, for example, in U.S. Pat. Nos. 4,238,343 and 4,045,507, and in Onopchenko, et al., $BF_3$-Catalyzed Oligomerization of Alkenes (Structures, Mechanisms and Properties) 183rd ACS Natl. Meet (Las Vegas, March 1982). Ind. Eng. Chem., Prod. Res. Dev., 22(2), 182-91 (June 1983). These alpha olefin oligomers are 75% or more di- or tri-substituted at the olefin site. For example, an alpha olefin trimer has a structure that can be represented by:

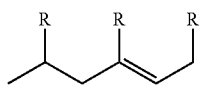

wherein: R=n−2, and n is the carbon number of the starting alpha olefin.

Alpha olefin oligomers are substantially straight-chain.

Preferred alpha olefin oligomers (AOO's) are derived from $C_8$ to $C_{20}$ alpha olefins, more preferably, $C_{10}$ to $C_{14}$ alpha olefins. Preferred AOO's are dimers, trimers, tetramers and pentamers or mixtures thereof. Preferably, the alkyl group of the instant carboxylates is derived from alpha olefin oligomers selected from the group consisting of: $C_{10}$ dimers and $C_{12}$ dimers.

The preferred alkyl hydroxyaromatic group of the carboxylate employed in this invention is derived from the corresponding alkylhydroxyaromatic of Formula I below:

(I)

wherein R is a substantially straight-chain alkyl group of from 16 to 40 carbon atoms. Preferably, R is a substantially straight-chain alkyl group of from 20 to 28 carbon atoms.

The alkylphenols of Formula I above are prepared by reacting the appropriate olefin or olefin mixture with phenol in the presence of an alkylating catalyst at a temperature of from about 60° C. to 200° C., and preferably 125° C. to 180° C. either neat or in an essentially inert solvent at atmospheric pressure. A preferred alkylating catalyst is a sulfonic acid catalyst such as Amberlyst 15® or Amberlyst 36® available from Rohm and Haas, Philadelphia, Pa. Molar ratios of reactants can be employed. When molar ratios are employed, the reaction yields a mixture of dialkylhydroxyaromatic, monoalkylhydroxyaromatic and unreacted hydroxyaromatic compounds. As noted above, dialkylhydroxyaromatic and monoalkylhydroxyaromatic hydroxyaromatic compounds can be used to prepare the additives used in the compositions of this invention whereas the unreacted hydroxyaromatic hydroxyaromatic compounds is preferably removed from the post reaction mixture via conventional techniques. Alternatively, molar excess of phenol can be employed, i.e., 2 to 2.5 equivalents of phenol for each equivalent of olefin with unreacted hydroxyaromatic compounds recycled. The latter process maximizes monoalkyl hydroxyaromatic compounds. Examples of inert solvents include benzene, toluene, chlorobenzene and 250 thinner which is a mixture of aromatics, paraffins and naphthenes.

Useful AOO derived alkyl hydroxyaromatic compounds have average molecular weights in the range of 350 to 790, and average alkyl carbon numbers ranging from 16 to 50, and preferably from 20 to 40.

The alkylhydroxyaromatic compounds derived from the AOO's are substantially liquid at ambient temperatures.

Alternative methods of preparing the alkylhydroxyaromatic compounds used herein are also contemplated. "Pinwheel" alkyl phenols can be synthesized by any number of methods. These methods typically rely upon either performing the entire alkyl moiety prior to alkylation of the phenol or subsequently elaborating a preformed alkyphenol wherein the alkyl group has the requisite functionality for further development to a pinwheel alkyl phenol. Thus, one could alkylate phenol with either a pinwheel olefin or a corresponding alcohol, or alkyl halide, such as a chloride or bromide.

Acid Catalyst

In one embodiment, the alkylated hydroxyaromatic compound may be prepared using strong acid catalysts (Bronsted or Lewis acids). The term "strong acid" refers to an acid having a $pK_a$ of less than about 4. The term "strong acid" is also meant to include mineral acids stronger than hydrochloric acid and organic acids having a Hammett acidity value of at least minus 10 or lower, preferably at least minus 12 or lower, under the same conditions employed in context with the herein described invention. The Hammett acidity function is defined as:

$$H_o = pK_{BH+} - \log(BH^+/B)$$

where B is the base and $BH^+$ its protonated form, $pK_{BH+}$ is the dissociation constant of the conjugate acid and $BH^+/B$ is the ionization ratio; lower negative values of $H_o$ correspond to greater acid strength.

In one embodiment, the strong acid catalyst is selected from a group consisting of hydrochloric acid, hydrofluoric acid, hydrobromic acid, sulfuric acid, perchloric acid, trifluoromethane sulfonic acid, fluorosulfonic acid, and nitric acid. Most preferred, the strong acid catalyst is hydrofluoric acid.

The alkylation process may be carried out in a batch or continuous process. The strong acid catalyst may be recycled when used in a continuous process. The strong acid catalyst may be recycled or regenerated when used in a batch process or a continuous process.

The strong acid catalyst may be regenerated after it becomes deactivated (i.e., the catalyst has lost all or some portion of its catalytic activity). Methods that are well known in the art may be used to regenerate the deactivated hydrofluoric acid catalyst.

Other suitable acid catalysts include sulfonic acid ion exchange resins, such as the class of materials identified as Amberlyst® that can be obtained from Rohm and Haas Corporation. Other sulfonic acid ion exchange resins are suitable. Other solid acid catalyst that may be employed include at least one metal oxide, which is selected from the group consisting of natural zeolites, synthetic zeolites, synthetic molecular sieves, and clays. Preferably, the second solid, acidic catalyst comprises the acid forms of an acidic clay, or an acidic molecular sieve or a zeolite having an average pore size of at least 6.0 angstroms. Such zeolites include zeolite Y, beta, SSZ-25, SSZ-26, and SSZ-33. Other possible catalysts include L zeolite, mordenite, boggsite, cloverite, VPI-5, MCM-41, MCM-36, SAPO-8, SAPO-5, MAPO-36, SAPO40, SAPO-41, MAPSO-46, CoAPO-50, hexagonal faujasite (EMC-2), gmelinite, mazzite (omega zeolite), offretite, ZSM-18, and ZSM-12. These catalysts are discussed in Rosemarie Szostak's Handbook of Molecular Sieves (New York, Van Nostrand Reinhold, 1992).

The alkylation process may be carried out in a batch or continuous process. The strong acid catalyst may be recycled when used in a continuous process.

Process for Preparing the Alkylated Aromatic Compound

In one embodiment of the present invention, the alkylation process is carried out by reacting a first amount of at least one hydroxyaromatic compound or a mixture of hydroxyaromatic compounds with a mixture of alpha olefin oligomers in the presence of a strong acid catalyst, such as hydrofluoric acid, in a reactor in which agitation is maintained, thereby producing a reaction product. The strong acid catalyst may be recycled to the reactor(s) in a closed loop cycle. The reaction product is further treated to remove excess un-reacted hydroxyaromatic compounds and, optionally, olefinic compounds from the desired alkylate product. The excess hydroxyaromatic compounds may also be recycled to the reactor(s).

The total charge mole ratio of hydrofluoric acid to the mixture of olefin compounds is about 1.0 to 1.

The total charge mole ratio of the aromatic compound to the mixture of olefin compounds is about 7.5 to 1.

The alkylation process may be carried out at temperatures from about 0° C. to about 100° C. The process is carried out under sufficient pressure that a substantial portion of the feed components remain in the liquid phase. Typically, a pressure of 0 to 150 psig is satisfactory to maintain feed and products in the liquid phase.

In a continuous alkylation process, the alkylation may be carried out using a fixed bed containing the solid acid catalyst. The continuous process may be carried out between 40 and 180 degrees Celsius and typically operates at atmospheric pressure.

The hydrocarbon feed for the alkylation process may comprise a mixture of hydroxyaromatic compounds and a mixture of alpha olefin oligomers in which the molar ratio of hydroxyaromatic compounds to alpha olefin oligomers is from about 0.5:1 to about 50:1 or more. In the case where the molar ratio of hydroxyaromatic compounds to alpha olefin oligmers is >1.0 to 1, there is an excess amount of hydroxyaromatic compounds present. Preferably an excess of hydroxyaromatic compounds is used to increase reaction rate and improve product selectivity. When excess hydroxyaromatic compounds are used, the excess un-reacted hydroxyaromatic in the reactor effluent can be separated, e.g. by distillation, and recycled to the reactor.

Neutralization Step

The alkylated hydroxyaromatic compound, as described above, is neutralized using an alkali metal base, including but not limited to oxides or hydroxides of lithium, sodium or potassium. In a preferred embodiment, potassium hydroxide is preferred. In another preferred embodiment, sodium hydroxide is preferred. Neutralization of the alkylated hydroxyaromatic compound takes place, preferably, in the presence of a light solvent, such as toluene, xylene isomers, light alkylbenzene or the like, to form an alkali metal salt of the alkylated hydroxyaromatic compound. In one embodiment, the solvent forms an azeotrope with water. In another embodiment, the solvent may also be a mono-alcohol such as 2-ethylhexanol. In this case, the 2-ethylhexanol is eliminated by distillation before carboxylation. The objective with the solvent is to facilitate the elimination of water.

This step is carried out at a temperature high enough to eliminate water. In one embodiment, the product is put under a slight vacuum in order to require a lower reaction temperature.

In one embodiment, xylene is used as a solvent and the reaction conducted at a temperature between 130° C. and 155° C., under an absolute pressure of 800 mbar ($8*10^4$ Pa).

In another embodiment, 2-ethylhexanol is used as solvent. As the boiling point of 2-ethylhexanol (184° C.) is significantly higher than xylene (140° C.), the reaction is conducted at a temperature of at least 150.degree. C.

The pressure is reduced gradually below atmospheric in order to complete the distillation of water reaction. Preferably, the pressure is reduced to no more than 70 mbar ($7*10^3$ Pa).

By providing that operations are carried out at a sufficiently high temperature and that the pressure in the reactor is reduced gradually below atmospheric, the neutralization reaction is carried out without the need to add a solvent and forms an azeotrope with the water formed during this reaction). In this case, temperature is heated up to 200° C. and then the pressure is reduced gradually below atmospheric. Preferably the pressure is reduced to no more than 70 mbar ($7*10^3$ Pa).

Elimination of water is done over a period of at least 1 hour, preferably at least 3 hours.

The quantities of reagents used should correspond to the following molar ratios: alkali metal base:alkylated hydroxyaromatic compound from about 0.5:1 to 1.2:1, preferably from about: 0.9:1 to 1.05:1 solvent:alkylated hydroxyaromatic compound (vol:vol) from about 0.1:1 to 5:1, preferably from about 0.3:1 to 3:1 B.

Carboxylation

The carboxylation step is conducted by simply bubbling carbon dioxide ($CO_2$) into the reaction medium originating from the preceding neutralization step and is continued until at least 50% of the starting alkylated hydroxyaromatic compound has been converted to alkylhydroxybenzoic acid (measured as hydroxybenzoic acid by potentiometric determination).

At least 50 mole %, preferably 75 mole %, more preferably 85 mole % of the starting alkylated hydroxyaromatic compound is converted to alkylhydroxylbenzoate using carbon dioxide at a temperature between about 110° C. and 200° C. under a pressure within the range of from about atmospheric to 15 bar ($15*10^5$ Pa), preferably from 1 bar ($1*10^5$ Pa) to 5 bar ($5*10^5$ Pa), for a period between about 1 and 8 hours.

In one variant with potassium salt, temperature is preferably between about 125° C. and 165° C. and more preferably between 130° C. and 155° C., and the pressure is from about atmospheric to 15 bar ($15*10^5$ Pa), preferably from about atmospheric to 4 bar ($4*10^5$ Pa).

In another variant with sodium salt, temperature is directionally lower preferably between from about 110° C. and 155° C., more preferably from about 120° C. and 140° C. and the pressure from about 1 bar to 20 bar ($1*10^5$ to $20*10^5$ Pa), preferably from 3 bar to 15 bar ($3*10^5$ to $15*10^5$ Pa).

The carboxylation is usually carried out, diluted in a solvent such as hydrocarbons or alkylate, e.g., benzene, toluene, xylene and the like. In this case, the weight ratio of solvent: hydroxybenzoate (i.e., alkali metal salt of the alkylated hydroxyaromatic compound) is from about 0.1:1 to 5:1, preferably from about 0.3:1 to 3:1.

In another variant, no solvent is used. In this case, carboxylation is conducted in the presence of diluent oil in order to avoid a too viscous material.

The weight ratio of diluent oil:alkylhydroxybenzoate is from about 0.1:1 to 2:1, preferably from about 0.2:1 to 1:1 and more preferably from about 0.2:1 to 0.5:1.

Acidification

The alkylated hydroxyaromatic carboxylic acid alkali metal salt produced above is then contacted with at least one acid capable of converting the alkali metal salt to an alkylated hydroxyaromatic carboxylic acid. Such acids are well known in the art to acidify the aforementioned alkali metal salt.

Overbasing

Overbasing of the alkylated hydroxyaromatic carboxylic acid may be carried out by any method known by a person skilled in the art to produce an overbased alkylated hydroxyaromatic carboxyate detergent.

In one embodiment of the invention, the overbasing reaction is carried out in a reactor by reacting the alkylated hydroxyaromatic carboxylic acid with lime (i.e., alkaline earth metal hydroxide) in the presence of carbon dioxide, in the presence of an aromatic solvent (i.e., xylene), and in the presence of a hydrocarbyl alcohol such as methanol.

The degree of overbasing may be controlled by the quantity of the alkaline earth metal hydroxide, carbon dioxide and the reactants added to the reaction mixture and the reaction conditions used during the carbonation process.

The weight ratios of reagents used (methanol, xylene, slaked lime and $CO_2$) will correspond to the following weight ratios: Xylene:slaked lime from about 1.5:1 to 7:1, preferably from about 2:1 to 4:1. Methanol:slaked lime from about 0.25:1 to 4:1, preferably from about 0.4:1 to 1.2:1. Carbon dioxide:slaked lime from a molar ratio about 0.5:1 to 1.3:1, preferably from about 0.7:1 to 1.0:1. $C_1$-$C_4$ carboxylic acid: alkaline metal base alkylhydroxybenzoate a molar ratio from about 0.02:1 to 1.5:1, preferably from about 0.1:1 to 0.7:1.

Lime is added as a slurry (i.e., as a pre-mixture of lime, methanol, xylene) and $CO_2$ is introduced over a period of 1 hour to 4 hours, at a temperature between about 20° C. and 65° C.

The quantity of lime and $CO_2$ are adjusted in order to obtain for a high overbased material (TBN>250) and crude sediment in the range of 0.4 volume % to 3 volume %, preferably in the range of 0.6 volume % to 1.8 volume %, without any deterioration of the performance.

For a middle overbased material (TBN from 100 to 250), the quantity of lime and $CO_2$ are adjusted in order to obtain a crude sediment in the range of 0.2 volume % to 1 volume %. The crude sediment without the use of $C_1$-$C_4$ carboxylic acid will range from about 0.8 volume % to 3 volume %.

Optionally, for each of the processes described above, pre-distillation, centrifugation and distillation may be utilized to remove solvent and crude sediment. Water, methanol and a portion of the xylene may be eliminated by heating between 110° C. to 134° C. This may be followed by centrifugation to eliminated unreacted lime. Finally, xylene may be eliminated by heating under vacuum in order to reach a flash point of at least about 160° C. as determined with the Pensky-Martens Closed Cup (PMCC) Tester described in ASTM D93.

Lubricating Oil Composition

The present invention also relates to lubricating oil compositions containing the overbased alkylated hydroxyaromatic carboxylate detergent of the present invention. Such lubricating oil compositions will comprise a major amount of a base oil of lubricating viscosity and a minor amount of the overbased alkylated hydroxyaromatic carboxylate detergent of the present invention.

Base oil as used herein is defined as a base stock or blend of base stocks which is a lubricant component that is produced by a single manufacturer to the same specifications (independent of feed source or manufacturer's location); that meets the same manufacturer's specification; and that is identified by a unique formula, product identification number, or both. Base stocks may be manufactured using a variety of different processes including but not limited to distillation, solvent refining, hydrogen processing, oligomerization, esterification, and rerefining. Rerefined stock shall be substantially free from materials introduced through manufacturing, contamination, or previous use. The base oil of this invention may be any natural or synthetic lubricating base oil fraction particularly those having a kinematic viscosity at 100° C. and about 4 centistokes (cSt) to about 20 cSt. Hydrocarbon synthetic oils may include, for example, oils prepared from the polymerization of ethylene, polyalphaolefin or PAO, or from hydrocarbon synthesis procedures using carbon monoxide and hydrogen gases such as in a Fisher-Tropsch process. A preferred base oil is one that comprises little, if any, heavy fraction; e.g., little, if any, lube oil fraction of viscosity about 20 cSt or higher at about 10° C. Oils used as the base oil will be selected or blended depending on the desired end use and the additives in the finished oil to give the desired grade of engine oil, e.g. a lubricating oil composition having an SAE Viscosity Grade of 0W, 0W-20, 0W-30, 0W-40, 0W-50, 0W-60, 5W, 5W-20, 5W-30, 5W-40, 5W-50, 5W-60, 10W, 10W-20, 10W-30, 10W-40, 10W-50, 15W, 15W-20, 15W-30, or 15W-40.

The base oil may be derived from natural lubricating oils, synthetic lubricating oils or mixtures thereof. Suitable base oil includes base stocks obtained by isomerization of synthetic wax and slack wax, as well as hydrocrackate base stocks produced by hydrocracking (rather than solvent extracting) the aromatic and polar components of the crude. Suitable base oils include those in all API categories I, II, III, IV and V as defined in API Publication 1509, 14th Edition, Addendum I, December 1998. Saturates levels and viscosity indices for Group I, II and III base oils are listed in Table I. Group IV base oils are polyalphaolefins (PAO). Group V base oils include all other base oils not included in Group I, II, III, or IV. Group III base oils are preferred.

TABLE I

Saturates, Sulfur and Viscosity Indices of Group I, II, III, IV and V Base Stocks

| Group | Saturates (as determined by ASTM D2007) | Viscosity Index | Sulfur (as determined by ASTM D4294, D2270, 4297 or 3120) |
|---|---|---|---|
| I | Less than 90% saturates and/or | Greater than or equal to 80 and | Greater than to 0.03% sulfur less than 120 |
| II | Greater than or equal to 90% | Greater than or equal to 80 and saturates and | less than or equal to 0.03% less than 120 sulfur |
| III | Greater than or equal to 90% | Greater than or equal to 120 saturates and | less than or equal to 0.03% sulfur |
| IV | All Polyalphaolefins (PAOs) | All Polyalphaolefins (PAOs) | All Polyalphaolefins (PAOs) |
| V | All others not included in Groups I, II, III, or IV | All others not included in Groups I, II, III, or IV | All others not included in Groups I, II, III, or IV |

Natural lubricating oils may include animal oils, vegetable oils (e.g., rapeseed oils, castor oils and lard oil), petroleum oils, mineral oils, and oils derived from coal or shale.

Synthetic oils may include hydrocarbon oils and halo-substituted hydrocarbon oils such as polymerized and interpolymerized olefins, alkylbenzenes, polyphenyls, alkylated diphenyl ethers, alkylated diphenyl sulfides, as well as their derivatives, analogues and homologues thereof, and the like. Synthetic lubricating oils also include alkylene oxide polymers, interpolymers, copolymers and derivatives thereof wherein the terminal hydroxyl groups have been modified by esterification, etherification, etc. Another suitable class of synthetic lubricating oils comprises the esters of dicarboxylic acids with a variety of alcohols. Esters useful as synthetic oils also include those made from $C_5$ to $C_{12}$ monocarboxylic acids and polyols and polyol ethers. Tri-alkyl phosphate ester oils such as those exemplified by tri-n-butyl phosphate and tri-iso-butyl phosphate are also suitable for use as base oils.

Silicon-based oils (such as the polyalkyl-, polyaryl-, polyalkoxy-, or polyaryloxy-siloxane oils and silicate oils) comprise another useful class of synthetic lubricating oils. Other synthetic lubricating oils include liquid esters of phosphorus-containing acids, polymeric tetrahydrofurans, polyalphaolefins, and the like.

The base oil may be derived from unrefined, refined, rerefined oils, or mixtures thereof. Unrefined oils are obtained directly from a natural source or synthetic source (e.g., coal, shale, or tar sand bitumen) without further purification or treatment. Examples of unrefined oils include a shale oil obtained directly from a retorting operation, a petroleum oil obtained directly from distillation, or an ester oil obtained directly from an esterification process, each of which may then be used without further treatment. Refined oils are similar to the unrefined oils except that refined oils have been treated in one or more purification steps to improve one or more properties. Suitable purification techniques include distillation, hydrocracking, hydrotreating, dewaxing, solvent extraction, acid or base extraction, filtration, and percolation, all of which are known to those skilled in the art. Rerefined oils are obtained by treating used oils in processes similar to those used to obtain the refined oils. These rerefined oils are also known as reclaimed or reprocessed oils and often are additionally processed by techniques for removal of spent additives and oil breakdown products.

Base oil derived from the hydroisomerization of wax may also be used, either alone or in combination with the aforesaid natural and/or synthetic base oil. Such wax isomerate oil is produced by the hydroisomerization of natural or synthetic waxes or mixtures thereof over a hydroisomerization catalyst.

It is preferred to use a major amount of base oil in the lubricating oil composition of the present invention. A major amount of base oil as defined herein comprises 40 wt or more. Preferred amounts of base oil comprise from about 40 wt % 97 wt %, preferably greater than from about 50 wt % to 97 wt %, more preferably from about 60 wt % to 97 wt % and most preferably from about 80 wt % to 95 wt % of the lubricating oil composition. (When weight percent is used herein, it is referring to weight percent of the lubricating oil unless otherwise specified.)

The overbased alkylated hydroxyaromatic carboxylate (i.e., overbased alkali metal alkylhydroxybenzoate) produced by the process of the present invention in the lubricating oil composition will be in a minor amount compared to the base oil of lubricating viscosity. Generally, it will be in an amount from about 1 wt % to 25 wt %, preferably from about 2 wt % to 12 wt % and more preferably from about 3 wt % to 8 wt %, based on the total weight of the lubricating oil composition.

Other Additive Components

The following additive components are examples of components that can be favorably employed in combination with the lubricating additive of the present invention. These examples of additives are provided to illustrate the present invention, but they are not intended to limit it.

(A) Ashless Dispersants

Alkenyl succinimides, alkenyl succinimides modified with other organic compounds, and alkenyl succinimides modified with boric acid, alkenyl succinic ester.

(B) Oxidation Inhibitors

1) Phenol type phenolic) oxidation inhibitors: 4,4'-methylenebis(2,6-di-tert-butylphenol), 4,4'-bis(2,6-di-tert-butylphenol), 4,4'-bis(2-methyl-6-tert-butylphenol), 2,2'-(methylenebis(4-methyl-6-tert-butyl-phenol), 4,4'-butylidenebis (3-methyl-6-tert-butylphenol), 4,4'-isopropylidenebis(2,6-di-tert-butylphenol), 2,2'-methylenebis(4-methyl-6-nonylphenol), 2,2'-isobutylidene-bis(4,6-dimethylphenol), 2,2'-methylenebis(4-methyl-6-cyclohexylphenol), 2,6-di-tert-butyl-4-methylphenol, 2,6-di-tert-butyl-4-ethylphenol, 2,4-dimethyl-6-tert-butyl-phenol, 2,6-di-tert-.alpha.-dimethylamino-p-cresol, 2,6-di-tert-4(N.N' dimethylaminomethylphenol), 4,4'-thiobis(2-methyl-6-tert-butylphenol), 2,2'- thiobis(4-methyl-6-tert-butylphenol), bis(3-methyl-4-hydroxy-5-tert-butylbenzyl)-sulfide, and bis(3,5-di-tert-butyl-4-hydroxybenzyl).

2) Diphenylamine type oxidation inhibitor: alkylated diphenylamine, phenyl-.alpha.-naphthylamine, and alkylated .alpha.-naphthylamine.

3) Other types: metal dithiocarbamate (e.g., zinc dithiocarbamate), and methylenebis(dibutyldithiocarbamate).

(C) Rust Inhibitors (Anti-Rust Agents)

1) Non ionic polyoxyethylene surface active agents: polyoxyethylene lauryl ether, polyoxyethylene higher alcohol ether, polyoxyethylene nonylphenyl ether, polyoxyethylene octylphenyl ether, polyoxyethylene octyl stearyl ether, polyoxyethylene oleyl ether, polyoxyethylene sorbitol monostearate, polyoxyethylene sorbitol mono-oleate, and polyethylene glycol monooleate.

2) Other compounds: stearic acid and other fatty acids, dicarboxylic acids, metal soaps, fatty acid amine salts, metal salts of heavy sulfonic acid, partial carboxylic acid ester of polyhydric alcohol, and phosphoric ester.

(D) Demulsifiers

Addition product of alkylphenol and ethyleneoxide, polyoxyethylene alkyl ether, and polyoxyethylene sorbitane ester.

(E) Extreme Pressure Agents (EP Agents)

Zinc dialkyldithiophosphate (Zn-DTP, primary alkyl type & secondary alkyl type), sulfurized oils, diphenyl sulfide, methyl trichlorostearate, chlorinated naphthalene, benzyl iodide, fluoroalkylpolysiloxane, and lead naphthenate.

(F) Friction Modifiers

Fatty alcohol, fatty acid, amine, borated ester, and other esters (G) Multifunctional Additives Sulfurized oxymolybdenum dithiocarbamate, sulfurized oxymolybdenum organo phosphorodithioate, oxymolybdenum monoglyceride, oxymolybdenum diethylate amide, amine-molybdenum complex compound, and sulfur-containing molybdenum complex compound.

(H) Viscosity Index Improvers

Polymethacrylate type polymers, ethylene-propylene copolymers, styrene-isoprene copolymers, hydrated styrene-isoprene copolymers, polyisobutylene, and dispersant type viscosity index improvers.

(I) Pour-Point Depressants

Polymethyl methacrylate.

(J) Foam Inhibitors

Alkyl methacrylate polymers and dimethyl silicone polymers.

(K) Metal Detergents

Sulfurized or unsulfurized alkyl or alkenyl phenates, alkyl or alkenyl aromatic sulfonates, calcium sulfonates, sulfurized or unsulfurized metal salts of multi-hydroxy alkyl or alkenyl aromatic compounds, alkyl or alkenyl hydroxy aromatic sulfonates, sulfurized or unsulfurized alkyl or alkenyl naphthenates, metal salts of alkanoic acids, metal salts of an alkyl or alkenyl multi-acid, and chemical and physical mixtures thereof.

Other embodiments will be obvious to those skilled in the art.

The following examples are presented to illustrate specific embodiments of this invention and are not to be construed in any way as limiting the scope of the invention.

EXAMPLE 1

Low Temperature Performance of C20-24 Carboxylates in an Automotive Engine Oil Formulation Table 1.1 illustrates the low temperature performance of five carboxylate detergents as measured in the ASTM D 4684 (−35° C., MRV) test in a fully formulated automotive engine oil prepared using the following automotive engine oil additive package and base oil blend:

TABLE 1

Automotive Engine Oil Additive Package

| Additive | Treat Rate |
|---|---|
| Borated Bis-Succinimide | 3.0 wt. % |
| Post Treated (Ethylene Carbonate) Bis-Succinimide | 5.0 wt. % |
| Non-Carbonated Calcium Sulfonate | 8 mmol Ca/kg in finished oil |
| Post Treated (PthalicAcid) Bis-Succinimide | 0.4 wt. % |
| Zinc Dithiophosphate | 12.5 mmol P/kg in finished oil |
| Molybdenum Succinimide Complex | 0.4 wt. % |
| Aminic Antioxidant | 0.5 wt. % |
| Phenolic Antioxidant | 0.5 wt. % |
| Foam Inhibitor | 30 ppm in finished oil |
| Carboxylate Detergent | 56 mmol Ca/kg in finished oil |

This package was blended at 15.2 weight % in the following base oil blend to make 5W40 multigrade finished oil:

TABLE 1.1

Base Oil Blends

| Component | % |
|---|---|
| Group III Base Oil 1 | 52.2 |
| Group III Base Oil 2 | 20.3 |
| Pourpoint Depressant | 0.3 |
| Viscosity Index Improver | 12.0 |

The data in Table 1.1 shows that when the alkylchain attached to the alkylphenol used to prepare the carboxylate detergent is more towards the center of the alkylchain; i.e. the amount of 4- and Higher Alkyl Chain Attachment is higher, the MRV performance is improved.

TABLE 1.2

| | Carboxylate | |
|---|---|---|
| | I | Comparative Carboxylate A |
| Carboxylate TBN | 350 | 357 |
| Alkylphenol Used to Prepare Carboxylate | Pinwheel I (Ex. 3) | A (Ex. 4) |
| Carbon Number of the Alkyl Tail in the Alkylphenol | 20-24 | 20-24 |
| % 4- and Higher Alkyl Chain Attachment to the Aromatic Ring in the Alkylphenol | 96.8 | 38.6 |
| % Branching in the Olefin Used to Prepare the Alkylphenol | 82.1 | 6.8 |
| MRV Results | | |
| Yield Stress (Pa) | 0 < Y <= 35 | Y > 350 |
| Viscosity (cP@ −35° C. | 31,905 | Frozen |

EXAMPLE 2

C10-12 Dimer Olefin

A sample of unhydrogenated C10-12 Normal Alpha Olefin (NAO) dimer was obtained from Chevron Phillips Chemical Company. Analysis by GLPC showed to be composed of approximately 84% C10 dimer and 16% C12 dimer olefin.

EXAMPLE 3

Preparation of Pinwheel Alkylphenol I

To a 10 liter, glass, four neck flask fitted with a mechanical stirrer, reflux condenser and thermocouple under a dry nitrogen atmosphere was charged 2500 grams of melted phenol (26.6 moles) followed by 1490 grams (5.2 moles) of the C10-12 Dimer Olefin of Example 2. To this gently stirring mixture was added 490 grams of Amberlyst 36® acidic ion exchange resin obtained from Rohm and Hass (dried approximately 25 hours in an oven at 110° C.). The reaction temperature was increased to 120° C. and held for about 87.5 hours at which time the conversion was 81.0% (by Supercritical Fluid Chromatography). An additional 100 grams of Amberlyst 36 catalyst was added to the reaction flask and the reaction was held at 120° C. for 29.5 hours at which time the conversion was 83.7% (by Supercritical Fluid Chromatography). The product was filtered through a Buchner funnel with the aid of vacuum and the filtrate combined with that of previous reactions to afford approximately 1.3 kg of product. This product was vacuum distilled (98 to 108° C. at 50 Torr vacuum, then 94° C. at 30 Ton vacuum and then finally 94-204° C. at 1.0 Ton vacuum to afford 8638 grams of alkylphenol I with the following properties: 12.8% paraffin, 6.0% Di-alkylate by Supercritical Fluid Chromatography; 58% para-alkyl isomer by IR; 1.1% Ether, 3.7% Di-Alkylate, 54.2% para-alkyl-isomer, 0.03% free phenol and Mn=343 by HPLC; 12.7% alkanes by GCMS.

EXAMPLE 4

Preparation of Alkylphenol A

The alkylphenol A was prepared as in Example 3 using unisomerized C20-24 NAO obtained from Chevron Phillips Chemical Company. Alkylphenol A had the following properties: 2.7% Unreacted olefin/paraffin, 7.1% Di-alkylate by SFC; 40% para-alkyl-isomer by IR; 2.2% Ether, 4.9% Di-alkylate, 36.9% para-alkyl-isomer, 0.5% free phenol and Mn=394 by HPLC.

EXAMPLE 5

Determination of the Nature of the Alkylphenyl Group

GLPC using Mass Spectrometric detection (GCMS) was used to determine the nature of the alkylphenol substituent of the alkylphenols of Examples 3 and 4. Alkyl phenols tend to fragment during mass spectrometric analysis in such a manner that the larger of the alkyl chains on the benzylic position are eliminated to form a phenol ion species which then fragment to from the well known tropylium ion.

GCMS analysis of the Pinwheel alkylphenol of Example 3 shows a complex chromatogram consisting of a clump of peaks where baseline resolution of the peaks was not possible. However, averaging the MS scans of peaks over the entire clump showed formation of the phenol ion species in which only about 3.2% of the alkylphenyl groups are attached at the 2 and 3-position along the alkyl tail. Thus, approximately 96.8% of the alkyl groups are attached at the 4-position or higher along the hydrocarbon backbone.

GCMS analysis of the alkylphenol from Example 4 reveals well resolved peaks in the gas chromatogram. Analysis of MS fragmentation pattern for these peaks indicated that approximately 61.4% to the alkylphenyl groups are attached at the 2 and 3-position along the alkyl tail. Thus, approximately only approximately 38.6% of the alkyl groups are attached at the 4-position or higher along the hydrocarbon backbone.

EXAMPLE 6

Neutralization of Pinwheel Alkylphenol I to Prepare the Corresponding Potassium Salt The Pinwheel alkylphenol I of Example 3 (1500 grams, 3.48 moles) was charged to a 4 liter round bottom, four neck flask equipped with a Dean Stark trap and condenser followed by 750 g of mixed xylenes and 0.2 g of foam inhibitor. The mixture was heated to 60° C. over 15 minutes with agitation and then 507.2 grams (4.53 moles corrected for purity) of 50 wt % aqueous KOH solution was added over 10 minutes. This mixture was then heated to 135° C. over 150 minutes. At the beginning of this temperature ramp to 135° C., the pressure was reduced to 450 mm Hg. The resulting refluxing xylenes were maintained at reflux for an additional 3 hours at which point 358.5 ml of water was recovered from the Dean Stark trap. The reaction was then cooled to room temperature and kept under an atmosphere of dry nitrogen. Analysis of this liquid showed the presence of water=106 ppm and Total Base Number=89.8.

EXAMPLE 7

Carboxylation of the Potassium Salt of Pinwheel Alkylphenol I

The potassium alkylphenol salt xylene solution obtained from Example 6 was heated to 80° C. and transferred to a 4 liter stainless steel pressure reactor. The contents of the reactor was heated to 140° C. and $CO_2$ was bubbled through the product until the reactor reached 3 bar of pressure. The reaction was held at 140° C. and a constant pressure of 3 bar of $CO_2$ for 4 hours. The contents of the reactor was cooled to approximately 100° C. to afford a xylene solution of the potassium carboxylate with the following properties: 29.5% xylene by mass balance; Carboxylic Acid=62.8 mg KOH/gram of sample by titration.

EXAMPLE 8

Acidification of the Potassium Carboxylate Derived from Pinwheel Alkylphenol I

The potassium carboxylate xylene solution (1100 grams) obtained from Example 7 was poured into a 4 liter, round bottom four neck flask fitted with a mechanical stirrer, reflux condenser, thermometer under a dry nitrogen atmosphere at room temperature followed by 622 grams of mixed xylenes. To this mixture was added 1209 grams of 10 wt. % aqueous $H_2SO_4$ over 30 minutes with stirring. During this time, the reaction was heated to 60° C. and held at 60° C. for 30 minutes. The product was transferred to a reparatory funnel and allowed to stand approximately 2 hours to allow phase separation at which time 1619.3 grams of the organic phase was obtained with the following properties: Carboxylic Acid=38.3 mg KOH/gram of sample by titration; 59.2% xylene by mass balance; Water=2600 ppm; K=94 ppm.

EXAMPLE 9

Overbasing of the Carboxylic Acid Derived from Pinwheel Alkylphenol Ito Prepare Carboxylate I The overbasing of the carboxylic acid is accomplished in two steps: Neutralization and Carbonation followed by Predistillation, Centrifugation and Final Distillation.

Neutralization and Carbonation

A slurry of lime (272.9 grams), methanol (226.7 grams) and mixed xylenes (370 grams) is prepared in a jacketed, glass, 4 liter, four neck reactor fitted with a mechanical stirrer, gas inlet tube and reflux condenser at room temperature. To this mixture was added 1325.3 grams of the carboxylic acid xylene solution obtained from Example 8 over 15 minutes with stirring while heating the mixture to 28° C. The temperature of the reaction is then heated to 40° C. over 15 minutes and then 13.9 grams of a mixture (50:50 by weight) of formic acid/acetic acid is added to the flask. The temperature of the reaction increased to 43° C. and was allowed to stir 5 minutes. The reaction mixture was then cooled to 30° C. over 20 minutes and then CO2 gas (9.8 grams) was added to the reaction over 11 minutes at which time the temperature increased to 32° C. CO2 (81.6 grams) was added to the reaction over 75 minutes and the reaction temperature increased to 48° C. A second slurry of lime (51.9 grams), methanol (42.9 grams) and mixed xylenes (260 grams) was added to the flask. CO2 (61.1 grams) was added to the reaction over 57 minutes at which time the reaction temperature increased to 60° C.

Predistillation, Centrifugation and Final Distillation

The methanol, water and a portion of the xylenes was removed by distillation. The reflux condenser to a distillation head and the reaction temperature was increased to 128° C. over 110 minutes. When the reaction reached 128° C., 422.5 grams of oil (100 Neutral) was added with stirring. A sample of the reaction showed a crude sediment=2.5 vol %. This product was centrifuged to remove the solids present (Alfa Laval Gyrotester) and the resulting solution vacuum distilled to removed the remaining xylenes (204° C. at 60 mbar) to afford the Carboxylate I with the following properties: % Ca=12.40%, Viscosity (100° C.)=49.4 cSt, Carboxylic Acid=38.8 mg KOH/gram of sample by titration and Potassium=108 ppm, Total Base Number=350.

EXAMPLE 10

Comparative Example

Preparation of Comparative Example B Carboxylate A from Alkylphenol A

The procedure in Examples 6, 7, 8 and 9 were followed to prepare the Comparative Carboxylate A starting with the alkylphenol A from Example 4 to afford the Comparative Carboxylate A with the following properties: % Ca=12.66%, Viscosity (100° C.)=52.5 cSt, Carboxylic Acid=35.7 mg KOH/gram of sample by titration and Potassium=136 ppm and Total Base Number=357.

What is claimed is:

1. A lubricating oil carboxylate-containing detergent additive with improved low temperature performance prepared by a process comprising
    (a) alkylating a hydroxyaromatic compound with at least one alpha olefin oligomer, derived from substpntially straight chain oligomers of $C_8$ to $C_{20}$ alpha olefins, to thereby produce an alkylhydroxyaromatic compound, and wherein at least 90% of the molecules in the alkyl-hydroxyaromatic compound have the alkyl group attached at the 4-position or higher from the terminus of the longest chain of the alkyl group, and further wherein the alkyl group comprises at least one hydrocarbon tail of at least 7 carbons;
    (b) neutralizing the resulting alkylated hydroxyaromatic compound with an alkali metal base to provide an alkali metal salt of the alkylated hydroxyaromatic compound;
    (c) carboxylating the alkali metal salt from step (b) with carbon dioxide thereby producing an alkylated hydroxyaromatic carboxylic acid alkali metal salt;
    (d) acidifying the salt produced in step tc) with acid to produce the alkylated hydroxyaromatic carboxylic acid; and
    (e) overbasing the alkylated hydroxyaromatic carboxylic acid with lime in the presence of carbon dioxide thereby producing an overbased alkylated hydroxyaromatic carboxylate detergent.

2. The carboxylate detergent of claim 1 wherein the alpha olefin oligomer comprises a dirtier derived from $C_8$ to $C_{20}$ alpha olefins.

3. The carboxylate detergent of claim 1 wherein the alpha olefin oligomer comprises a dimer derived from $C_{10}$ to $C_{16}$ alpha olefins.

4. The carboxylate detergent of claim 1 wherein the alkali metal base is potassium hydroxide or sodium hydroxide.

5. The carboxylate detergent of claim 1 wherein in step (c) carbon dioxide is added to the reaction until at least 50% of the alkylated hydroxyaromatic compound has been converted to alkylhydroxybenzoic acid.

6. A lubricating oil composition comprising an oil of lubricating viscosity and the carboxylate detergent prepared by the process of claim 1.

7. The carboxylate detergent of claim 1 wherein at least 95% of the molecules in the alkylhydroxyaromatic compound have the alkyl group attached at the 4-position or higher from the terminus of the longest chain of the alkyl group, and further wherein the alkyl group comprises at least one hydrocarbon tail of at least 7 carbons.

8. A carboyxlate-containing detergent with improved low temperature performance having the following structure:

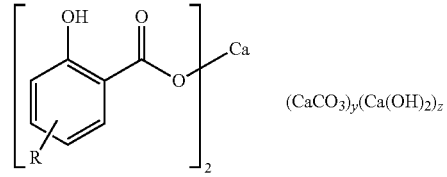

$(CaCO_3)_y(Ca(OH)_2)_z$ wherein R is a substantially straight-chain alkyl group of from about 16 to 40 carbon atoms, wherein the alkyl group is derived from substantially straight chain oligomers of $C_8$ to $C_{20}$ alpha olefins, and wherein at least 90% of the substantially straight-chain alkyl group has the alkyl group attached at the 4-position or higher from the terminus of the longest chain of the alkyl group, and further wherein the alkyl group comprises at least one hydrocarbon tail of at least 7 carbons and wherein v and z are independently whole or partial integers.

9. The carboxylate of claim 8 wherein the alkyl group is attached to the phenol ring at least 6 carbon atoms from the terminus of the longest chain of the alkyl group.

10. The carboxylate of claim 8 wherein R is a substantially straight-chain alkyl group of from 20 to 28 carbon atoms, wherein the alkyl group is derived from $C_{10}$ to $C_{14}$ alpha olefins.

11. The carboxylate of claim 10 wherein R is a substantially straight-chain alkyl group of 20 carbon atoms, derived from a $C_{10}$ dimer.

* * * * *